(12) United States Patent
Cavazzoni (10) Patent No.: US 7,591,850 B2
(45) Date of Patent: Sep. 22, 2009

(54) SURGICAL METHODS FOR ANCHORING AND IMPLANTING TISSUES

(75) Inventor: Pier Alfeo Zanotti Cavazzoni, Vimercate (IT)

(73) Assignee: ArthroCare Corporation, Austin, TX (US)

( * ) Notice: Subject to any disclaimer, the term of this patent is extended or adjusted under 35 U.S.C. 154(b) by 80 days.

(21) Appl. No.: 11/096,898

(22) Filed: Apr. 1, 2005

(65) Prior Publication Data

US 2006/0235516 A1    Oct. 19, 2006

(51) Int. Cl.
*A61F 2/08* (2006.01)
(52) U.S. Cl. ................................... 623/13.11
(58) Field of Classification Search ........... 606/72, 606/73, 139, 304, 62–67, 86 R, 88, 89, 96, 606/98, 99, 103, 104; 623/13.11–31.19, 623/13.2
See application file for complete search history.

(56) References Cited

U.S. PATENT DOCUMENTS

| 1,727,590 | A | 9/1929 | Thomas | 411/430 |
|---|---|---|---|---|
| 2,778,357 | A | 1/1957 | Leibinger et al. | 128/2 |
| 3,896,500 | A | 7/1975 | Rambert et al. | 623/13.14 |
| 3,905,356 | A | 9/1975 | Fletcher et al. | 600/587 |
| 3,973,277 | A | 8/1976 | Semple et al. | 623/13.14 |
| 3,974,621 | A | 8/1976 | Stang | 411/75 |
| 4,126,165 | A | 11/1978 | Guignard et al. | 142/56 |
| 4,149,277 | A | 4/1979 | Bokros | 623/13.2 |
| 4,187,558 | A | 2/1980 | Dahlen et al. | 623/13.14 |
| 4,204,544 | A | 5/1980 | Feldstein et al. | 600/375 |
| 4,275,717 | A | 6/1981 | Bolesky | |
| 4,309,778 | A | 1/1982 | Buechel et al. | 623/20.29 |
| 4,335,715 | A | 6/1982 | Kirkley | 606/87 |
| 4,347,024 | A | 8/1982 | Coldren | 411/11 |
| 4,406,281 | A | 9/1983 | Hubbard et al. | 128/846 |
| 4,530,357 | A | 7/1985 | Pawloski et al. | 606/180 |
| 4,573,448 | A | 3/1986 | Kambin | 606/170 |

(Continued)

FOREIGN PATENT DOCUMENTS

DE    9002844    1/1991

(Continued)

OTHER PUBLICATIONS

PCT Notification of the International Search Report and Written Opinion for PCT/US06/19100, 7 pgs, Mailed Sep. 27, 2007.

(Continued)

*Primary Examiner*—Eduardo C Robert
*Assistant Examiner*—Tara R George
(74) *Attorney, Agent, or Firm*—Matthew Scheele; Brian E. Szymczak (57) ABSTRACT

A surgical method of anchoring tissues in a target location, comprising tracking a cannulated dilator on a suture protruding from the target location and forming an enlarged opening in the target location using the cannulated dilator to enlarge the opening. A distal end of a guide wire is tracked through the dilator into the enlarged opening, and an anchoring device is slid on the guide wire to position the device in the enlarged opening. Advantageously, since the target location is dilated prior to receiving the anchoring device therein, a soft tissue disposed at the target location can be dilated before being anchored, to avoid possible damage to the tissue by the implanting device.

15 Claims, 10 Drawing Sheets

U.S. PATENT DOCUMENTS

| | | | |
|---|---|---|---|
| 4,583,554 A | 4/1986 | Mittelman et al. | 600/587 |
| 4,600,005 A | 7/1986 | Hendel | 128/304 |
| 4,600,007 A | 7/1986 | Lahodny et al. | 606/174 |
| 4,708,132 A | 11/1987 | Silvestrini | |
| 4,712,542 A | 12/1987 | Daniel et al. | 606/96 |
| 4,759,350 A | 7/1988 | Dunn et al. | 606/82 |
| 4,776,851 A | 10/1988 | Bruchman et al. | 623/13.11 |
| 4,820,279 A | 4/1989 | Dedo | 604/290 |
| 4,910,901 A | 3/1990 | Boyar | 40/607 |
| 4,950,270 A | 8/1990 | Bowman et al. | 606/72 |
| 4,969,471 A | 11/1990 | Daniel et al. | 600/587 |
| 4,997,433 A | 3/1991 | Goble et al. | 606/64 |
| 5,037,422 A | 8/1991 | Hayhurst et al. | 606/72 |
| 5,037,426 A | 8/1991 | Goble et al. | 606/96 |
| 5,046,513 A | 9/1991 | Gatturna et al. | 128/898 |
| 5,112,338 A | 5/1992 | Anspach, III | 606/99 |
| 5,139,520 A | 8/1992 | Rosenberg | 606/87 |
| 5,147,361 A | 9/1992 | Ojima et al. | 606/61 |
| D330,591 S | 10/1992 | Rosenberg et al. | D24/147 |
| 5,152,790 A | 10/1992 | Rosenberg et al. | 623/13.14 |
| 5,170,800 A | 12/1992 | Smith et al. | 600/564 |
| 5,176,682 A | 1/1993 | Chow | 606/72 |
| 5,176,699 A | 1/1993 | Markham | 606/206 |
| 5,228,448 A | 7/1993 | Byrd | 600/490 |
| 5,251,646 A | 10/1993 | Bowen | 128/878 |
| 5,254,129 A | 10/1993 | Alexander | 606/170 |
| 5,258,003 A | 11/1993 | Ciaglia et al. | 606/185 |
| 5,258,016 A | 11/1993 | DiPoto et al. | 606/232 |
| 5,266,075 A * | 11/1993 | Clark et al. | 606/138 |
| 5,303,472 A | 4/1994 | Mbanugo | 30/124 |
| 5,306,301 A | 4/1994 | Graf et al. | 623/13 |
| 5,314,429 A | 5/1994 | Goble | 606/96 |
| 5,324,308 A | 6/1994 | Pierce | 606/232 |
| 5,330,468 A | 7/1994 | Burkhart | 606/96 |
| 5,350,380 A * | 9/1994 | Goble et al. | 606/80 |
| 5,350,383 A | 9/1994 | Schmieding et al. | 606/96 |
| 5,364,400 A | 11/1994 | Rego, Jr. et al. | 606/72 |
| 5,383,471 A | 1/1995 | Funnell | 600/564 |
| 5,391,169 A | 2/1995 | McGuire | 606/79 |
| 5,393,302 A | 2/1995 | Clark et al. | 606/72 |
| RE34,871 E | 3/1995 | McGuire et al. | 606/73 |
| 5,395,375 A | 3/1995 | Turkel et al. | 606/83 |
| 5,405,359 A | 4/1995 | Pierce | 606/232 |
| 5,408,359 A | 4/1995 | Ferrett et al. | 359/601 |
| 5,423,860 A | 6/1995 | Lizardi et al. | 606/232 |
| 5,472,452 A | 12/1995 | Trott | 606/232 |
| 5,475,553 A | 12/1995 | Saliba | 360/122 |
| 5,489,292 A | 2/1996 | Tovey et al. | 606/207 |
| 5,529,424 A | 6/1996 | Neubert et al. | 403/298 |
| 5,556,411 A | 9/1996 | Taoda et al. | 606/185 |
| 5,562,664 A | 10/1996 | Durlacher et al. | 606/96 |
| 5,591,190 A | 1/1997 | Yoon | 606/185 |
| 5,591,232 A | 1/1997 | Rahimi et al. | 128/898 |
| 5,601,562 A | 2/1997 | Wolf et al. | 606/86 |
| 5,609,634 A | 3/1997 | Voydeville | 623/13.11 |
| 5,618,314 A | 4/1997 | Harwin et al. | 606/232 |
| 5,620,001 A | 4/1997 | Byrd et al. | 606/202 |
| 5,626,609 A | 5/1997 | Zvenyatsky et al. | 606/208 |
| 5,632,748 A | 5/1997 | Beck et al. | |
| 5,643,266 A | 7/1997 | Li | |
| 5,643,273 A | 7/1997 | Clark | 606/96 |
| 5,645,588 A | 7/1997 | Graf et al. | 606/151 |
| 5,647,874 A | 7/1997 | Hayhurst | 606/72 |
| 5,651,368 A | 7/1997 | Napolitano et al. | 600/490 |
| 5,674,224 A | 10/1997 | Howell et al. | 606/88 |
| 5,683,359 A | 11/1997 | Farkas et al. | 604/22 |
| 5,683,406 A | 11/1997 | Altobelli et al. | 606/170 |
| 5,683,471 A | 11/1997 | Incavo et al. | 128/898 |
| 5,707,395 A | 1/1998 | Li | |
| 5,713,897 A | 2/1998 | Goble et al. | 606/53 |
| 5,725,541 A | 3/1998 | Anspach et al. | |
| 5,733,307 A | 3/1998 | Dinsdale | 606/232 |
| 5,735,867 A | 4/1998 | Golser et al. | |
| 5,769,894 A | 6/1998 | Ferragamo | 606/148 |
| 5,782,749 A | 7/1998 | Riza | 600/117 |
| 5,788,701 A | 8/1998 | McCue | 606/88 |
| 5,791,350 A | 8/1998 | Morton | 600/590 |
| 5,797,963 A | 8/1998 | McDevitt | 606/232 |
| 5,813,808 A | 9/1998 | Wu | |
| 5,814,070 A | 9/1998 | Borzone et al. | 606/232 |
| 5,840,078 A | 11/1998 | Yerys | |
| 5,871,504 A | 2/1999 | Eaton et al. | 606/232 |
| 5,891,150 A | 4/1999 | Chan | 606/96 |
| 5,891,168 A | 4/1999 | Thai | 606/232 |
| 5,895,425 A | 4/1999 | Grafton et al. | 606/73 |
| 5,911,695 A | 6/1999 | Watkins et al. | 600/553 |
| 5,913,860 A | 6/1999 | Scholl | 606/100 |
| 5,918,604 A | 7/1999 | Whelan | 128/898 |
| 5,935,129 A | 8/1999 | McDevitt et al. | 606/72 |
| 5,984,966 A | 11/1999 | Kiema et al. | 623/13.14 |
| 5,989,253 A | 11/1999 | Bigliardi | 606/72 |
| 6,015,412 A | 1/2000 | Mifsud | |
| 6,056,752 A | 5/2000 | Roger | 623/13.12 |
| 6,068,648 A | 5/2000 | Cole et al. | 606/232 |
| D426,305 S | 6/2000 | Hein | D24/147 |
| 6,080,154 A | 6/2000 | Reay-Young et al. | |
| 6,086,591 A | 7/2000 | Bojarski | 606/64 |
| 6,099,568 A | 8/2000 | Simonian et al. | 623/13.11 |
| 6,110,207 A | 8/2000 | Eichhorn et al. | 623/13.14 |
| 6,117,161 A | 9/2000 | Li et al. | 606/232 |
| 6,132,433 A * | 10/2000 | Whelan | 606/72 |
| 6,146,406 A | 11/2000 | Shluzas et al. | 606/232 |
| 6,146,407 A | 11/2000 | Krebs | 606/232 |
| 6,214,007 B1 | 4/2001 | Anderson | |
| 6,221,107 B1 | 4/2001 | Steiner et al. | |
| 6,224,603 B1 | 5/2001 | Marino | 606/79 |
| 6,355,066 B1 | 3/2002 | Kim | |
| 6,402,757 B1 * | 6/2002 | Moore et al. | 606/80 |
| 6,440,134 B1 | 8/2002 | Zaccherotti et al. | |
| 6,478,753 B2 | 11/2002 | Reay-Young | |
| 6,517,542 B1 | 2/2003 | Papay et al. | 606/232 |
| 6,517,578 B2 | 2/2003 | Hein | |
| 6,533,802 B2 | 3/2003 | Bojarski et al. | 606/232 |
| 6,533,816 B2 | 3/2003 | Sklar | |
| 6,544,273 B1 | 4/2003 | Harari et al. | |
| 6,554,553 B2 | 4/2003 | Freedland | 411/392 |
| 6,562,071 B2 | 5/2003 | Jarvinen | |
| 6,599,289 B1 | 7/2003 | Bojarski et al. | 606/60 |
| 6,652,560 B1 | 11/2003 | Gerke et al. | |
| 6,685,728 B2 | 2/2004 | Sinnott et al. | 606/232 |
| 6,736,847 B2 | 5/2004 | Reay-Young et al. | |
| 6,802,862 B1 | 10/2004 | Roger et al. | |
| 6,808,528 B2 * | 10/2004 | Justin | 606/72 |
| 6,878,166 B2 * | 4/2005 | Clark et al. | 623/13.12 |
| 7,001,429 B2 | 2/2006 | Ferguson | 623/13.14 |
| 7,063,717 B2 | 6/2006 | Pierre et al. | 606/232 |
| 7,083,647 B1 | 8/2006 | Sklar et al. | 623/13.14 |
| D547,451 S | 7/2007 | Asfora | D24/146 |
| 7,285,121 B2 | 10/2007 | Braun et al. | 606/279 |
| 7,338,492 B2 | 3/2008 | Singhatat et al. | 606/232 |
| 2002/0038123 A1 | 3/2002 | Visotsky et al. | 606/73 |
| 2004/0193167 A1* | 9/2004 | Tucciarone et al. | 606/73 |
| 2005/0075636 A1 | 4/2005 | Gotzen | 606/72 |
| 2005/0192582 A1 | 9/2005 | Reay-Young | |
| 2005/0222619 A1 | 10/2005 | Dreyfuss et al. | 606/72 |
| 2006/0178673 A1 | 8/2006 | Curran | |
| 2006/0253119 A1 | 11/2006 | Berberich et al. | 606/72 |
| 2006/0271059 A1 | 11/2006 | Reay-Young et al. | |
| 2006/0276841 A1 | 12/2006 | Barbieri et al. | 606/232 |
| 2007/0021751 A1 | 1/2007 | Reay-Young et al. | |
| 2007/0213730 A1 | 9/2007 | Martinek et al. | 606/72 |
| 2007/0260249 A1 | 11/2007 | Boyajian et al. | 606/72 |
| 2008/0275553 A1 | 11/2008 | Wolf et al. | 623/13.14 |
| 2008/0288069 A1 | 11/2008 | Wolf et al. | 606/301 |

FOREIGN PATENT DOCUMENTS

| | | |
|---|---|---|
| DE | 29607352 | 9/1996 |
| EP | 238223 | 9/1987 |
| EP | 279129 | 8/1988 |
| EP | 317406 | 5/1989 |
| EP | 379789 | 11/1989 |
| EP | 346469 | 12/1989 |
| EP | 574707 | 12/1993 |
| EP | 619982 | 3/1994 |
| EP | 0 674 880 | 3/1995 |
| EP | 706780 | 4/1996 |
| EP | 0865774 | 9/1998 |
| EP | 1066805 | 6/2000 |
| EP | 1180351 | 2/2002 |
| FR | 2395012 | 1/1979 |
| FR | 2590792 | 6/1987 |
| FR | 2683715 | 5/1993 |
| FR | 2725615 | 4/1996 |
| FR | 2732211 | 4/1996 |
| GB | 2288739 | 11/1995 |
| GB | 2337463 | 11/1999 |
| SU | 1521465 | 11/1989 |
| WO | 93/25148 | 12/1993 |
| WO | 95/11631 | 5/1995 |
| WO | 96/03926 | 2/1996 |
| WO | 96/29029 | 9/1996 |
| WO | 96/39934 | 12/1996 |
| WO | 97/19634 | 6/1997 |
| WO | 97/20522 | 6/1997 |
| WO | 98/12991 | 4/1998 |
| WO | 98/12992 | 4/1998 |
| WO | 98/22048 | 5/1998 |
| WO | 98/38937 | 9/1998 |
| WO | 99/52472 | 10/1999 |
| WO | 99/59488 | 11/1999 |
| WO | 03/088874 | 10/2003 |

OTHER PUBLICATIONS

PCT Notification of the International Search Report and Written Opinion for PCT/US05/17382, 11 pgs, Mailed Oct. 23, 2007.
Smith & Nephew, "Arthroscopic Repair of a Bankart Lesion Using TAG Suture Anchors," 12 pgs, May 1996.
F.H. Fuh, et al., Anatomic ACL Double-Bundle Reconstruction, Orthopedic Technology Review vol. 7 No. 4, 6 pgs, 2005.
ArthroCare SportsMedicine Product Catalogue, 3.1 Knee (p. 44 p. 52), 4 pgs, Jul. 2005.
UK Search Report for GB 9915550 1 pg, Jun. 13, 2000.
UK Search Report for GB 9929599 1 pg, Oct. 12, 2000.
UK Search Report for GB 0116605 1 pg, Mar. 27, 2002.
UK Search Report for GB 0013037 1 pg, Mar. 20, 2001.
UK Search Report for GB 0208667 1 pg, Feb. 24, 2003.
European Search Report for EP 00113471 2 pgs, Jan. 26, 2001.
European Search Report for EP 00311077 2 pgs, Mar. 6, 2001.
European Search Report for EP 00830524 2 pgs, Aug. 8, 2001.
European Search Report for EP 01112516 2 pgs, Aug. 7, 2003.
European Search Report for EP 02013879 4 pgs, May 25, 2004.
European Search Report for EP 02014485 2 pgs, Nov. 4, 2003.
European Search Report for EP 97122626 2 pgs, Apr. 21, 1998.
European Search Report for EP 98301702 2 pgs, Jun. 23, 1998.
European Search Report for EP 99302529 2 pgs, Jul. 8, 1999.
PCT International Search Report for PCT/GB03/01606 3 pgs, Mailed Sep. 4, 2003.
PCT International Search Report for PCT/US06/04674 1 pg, Mailed Jul. 25, 2007.
PCT Notification of the International Search Report and Written Opinion for PCT/US05/01629, 6 pgs, Mailed Apr. 22, 2008.
PCT Written Opinion for PCT/US06/04674 4 pgs, Mailed Jul. 25, 2007.
UK Examination Report for GB0715476.8 3 pgs, Feb. 19, 2009.
Daily Updates, "ACL Reconstruction Using a Double-Looped Semitendinous and Gracilis (DLSTG) Hamstring Graft with the Bone Much Screw and Sasherloc Device from Arthrotec", <www.ptupdate.com/members/daily/Art012602.htm>, Printed Aug. 21, 2006.
"Graft Choices in ACL Reconstruction", Carleton Sports Medicine, <www.carletonsportsmed.com/graftacl.htm>, Printed Aug. 21, 2006.
"Distal Tendon Repair with the Lubbers Technique", Ortheon Medical, <www.ortheon.com/distal.htm>, Printed Aug. 21, 2006.

* cited by examiner

SURGICAL METHODS FOR ANCHORING AND IMPLANTING TISSUES

BACKGROUND OF THE INVENTION

1. Field of the Invention

This invention relates to surgical methods for anchoring and implanting devices and soft tissues in the body, such as in a knee joint. The invention also includes a surgical kit with instructions and tools for practicing the methods.

2. Description of the Prior Art

Surgical procedures for anchoring devices in a target location and for implanting soft tissues therein include procedures for replacing damaged tissues such as ligaments and tendons. For example, with reference to FIGS. 1-5, one such procedure is a technique for replacing a damaged anterior cruciate ligament (ACL) (24) in a human knee joint (20). Normally, in executing this procedure, a first step is to clean the surface of the joint and remove the damaged ACL. Thereafter, two co-axial passageways or tunnels (26, 28) are created in the knee joint: a generally upward-sloping tunnel (28) in the tibia (32) and a co-linear tunnel (26) in the condyle of a femur (30). To facilitate securing a replacement ligament (22) in the condyle of a femur, a third passageway or tunnel (34) is opened in the condyle of a femur, substantially transverse to tunnel (26) in the condyle of a femur.

Figure 1:
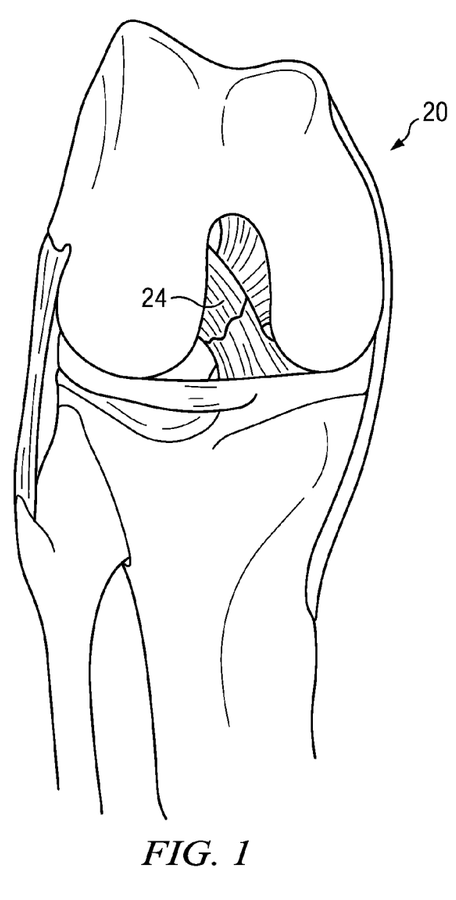
FIG. 1 is a front view schematic of an exposed knee joint showing a damaged anterior cruciate ligament.
Figure 2:
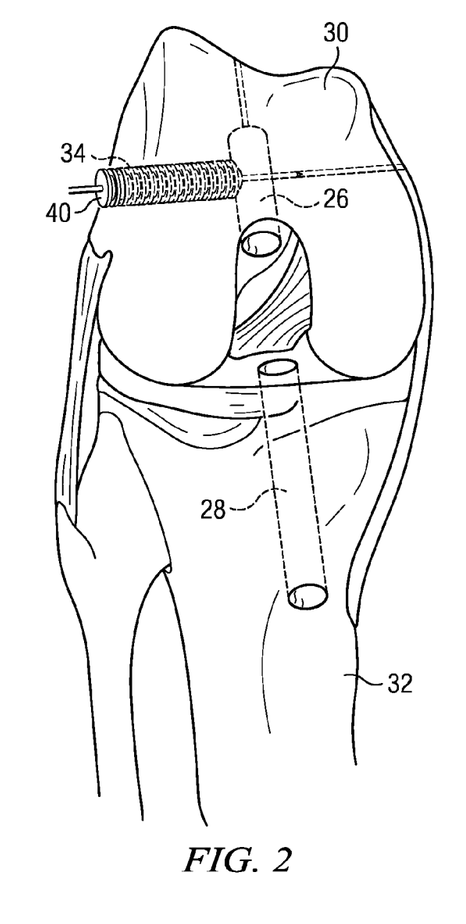
FIG. 2 is a front view schematic of an exposed knee joint of a knee joint showing tunnels for facilitating implants.
Figure 3:
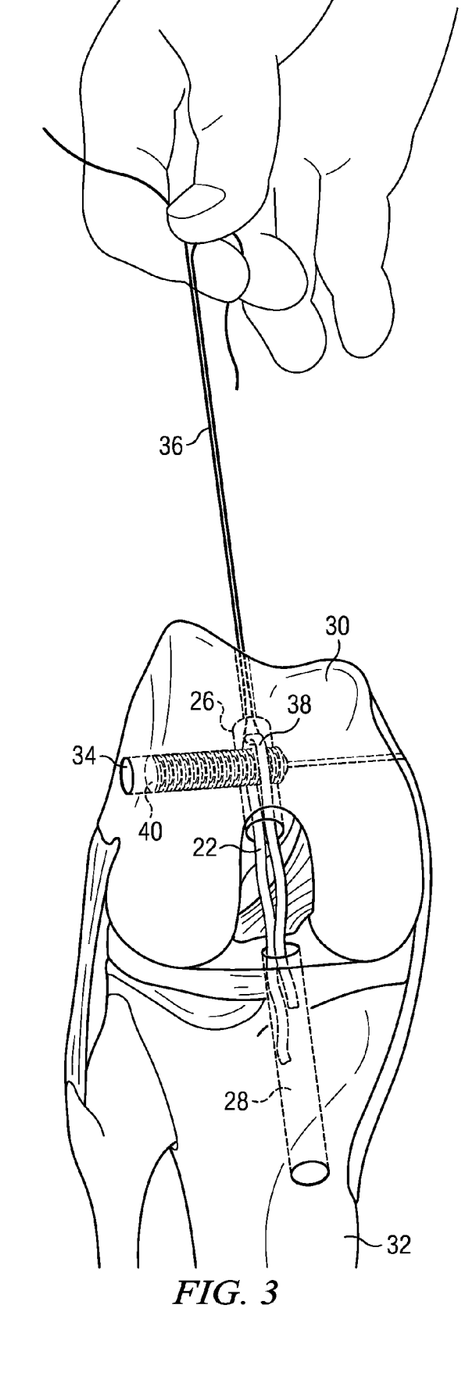
FIG. 3 is a front view schematic of an exposed knee joint showing inserting an implant.
Figure 4:
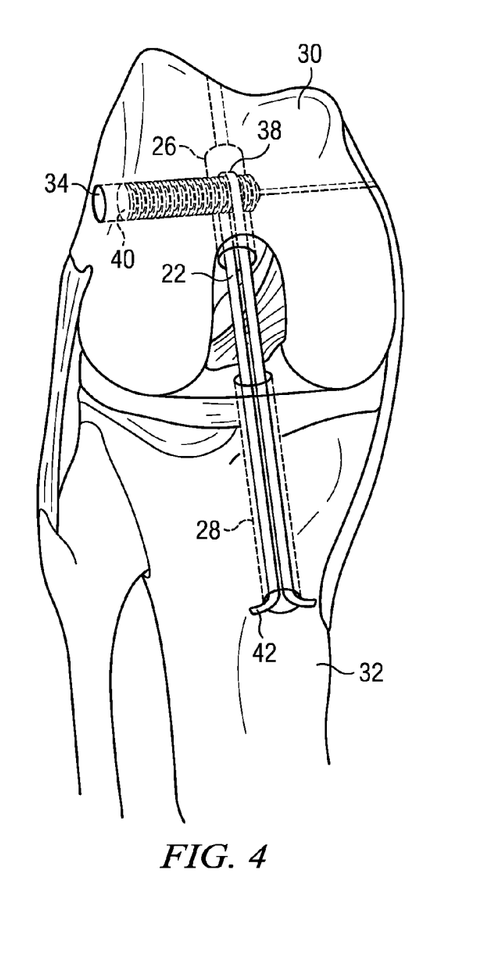
FIG. 4 is a front view schematic of an exposed knee joint showing securing an implant.

To secure the replacement ligament (22) in the condyle of a femur (34), the or graft loop is folded on a flexible suture (36) and pulled through tunnel (26) from the tibia, to a position where a fold (44) in the ligament or graft loop is substantially in line with the longitudinal axis of the transverse tunnel (34). Once in this position, an anchoring device (40) such as a screw is inserted through transverse tunnel (34) and tightened against the ligament, thus securing the ligament or graft loop in the condyle of a femur. This method is described in co-pending U.S. patent application Ser. No. 10/822,101, having a filing date of 8 Apr. 2004, hereby incorporated by reference in its entirety.

Figure 5:
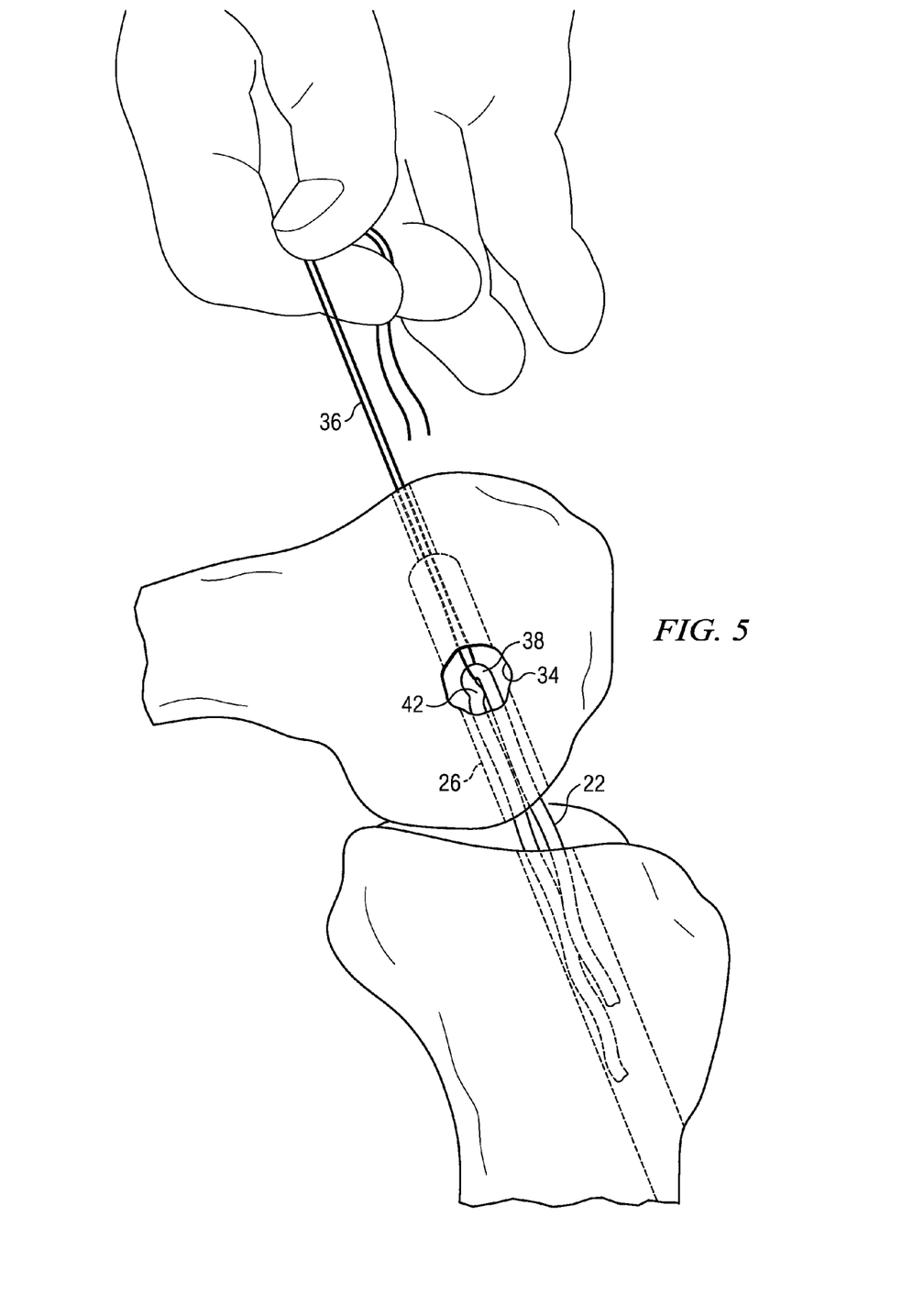
FIG. 5 is a side view schematic of a target location of an implant.

With reference to FIG. 5 which is a diagrammatic representation of a side view of the transverse tunnel (34) intersecting the generally upward tunnel (26) in a condyle of a femur (30), since the replacement ligament or graft loop (22) is folded on the suture (36) and pulled through the tunnel (26), an extended kink (42) may develop in the ligament or graft loop just in line with the longitudinal axis of the screw (not shown) in the intersecting tunnel (34). Thus, on attempting to engage the screw to secure the ligament or graft loop in the condyle femur, the ligament or graft loop being soft and easily damageable can be punctured and weakened at the fold as the screw or another instrument is forced through the kink.

Further, since this procedure is performed in a confined space with limited visibility and maneuverability, it is not easy for the surgeon to determine whether the ligament or graft loop is punctured as described, supra, and/or whether the device has passed through the kink to properly anchor the tissue. Consequently, there is a need for more reliable and efficient procedures for such surgery and to avoid causing potential trauma to the tissue. It is therefore an objective of this invention to address this need.

SUMMARY OF THE INVENTION

In one embodiment, the present invention, with reference to FIGS. 7-14, comprises a method of surgically anchoring a device in a target location. The method involves tracking a cannulated dilator on a suture protruding from the target location and using the dilator to form an enlarged opening in the target location, wherein the enlarged opening is created by the protruding suture and the cannulated dilator. With the dilator in position, the suture is removed and a guide wire or pin is inserted in the cannulated dilator such that the distal end of the guide wire is inserted into the enlarged opening through the cannulated dilator. The dilator is removed and an anchoring device is slid on the guide wire to position the device in the enlarged opening. Advantageously, since the target location is dilated prior to receiving the anchoring device therein, a soft tissue disposed at the target location can be dilated and anchored, thereby avoiding possible puncturing and damaging at the kink.

In another embodiment, the invention comprises a surgical method of securing an anchoring device in a target location whereby, a portion of a suture from the target location is grabbed through a passageway connected to the location. A cannulated dilator is tracked over the suture until a distal portion of the dilator penetrates the target location. The dilator is used to enlarge the target location to form an opening therein, after which the suture is removed. A guide wire is inserted through the cannulated dilator such that a distal end of the said guide wire resides, at least in part, within the enlarged opening. The dilator is retracted and an anchoring device is tracked over the guide wire to position the anchoring device, at least in part, within the opening. Advantageously, since the target location is dilated prior to receiving the anchoring device therein, a soft tissue at the target location can be dilated and implanted thereby avoiding possible damage to the soft tissue.

In another embodiment, the present invention comprises a surgical method of implanting soft tissue in a target location, comprising creating a first passageway in the target location. A soft tissue is folded on a flexible suture and pulled into the first passageway by the suture and a free end of the flexible suture is hooked from the first passageway through a passageway in the target location. Thereafter, a cannulated dilator is tracked over the free end of the suture until a distal portion of the dilator penetrates a location in the soft tissue through the passageway. The dilator is used to enlarge the soft tissue to form an opening. Thereafter, the suture is removed and a guide wire is inserted through the cannulated dilator such that the distal end of the guidewire resides, at least in part, within the opening. The dilator is then retracted and an anchoring device is tracked over the guide-wire such that the anchoring device is positioned, at least in part, within the opening to anchor the tissue in the target location.

In another embodiment, the present invention comprises a surgical kit including instructions for using the kit for performing the procedures that embody the methods of the present invention. Included in the kit are surgical hooks, sutures, screws, pins, and dilators.

Advantageously, with the present invention, since the target location is dilated with a guide member prior to receiving the anchoring device, e.g. a screw, the invention avoids the prior art problem whereby the screw or another tool, on being blindly forced through a kink of the ligament or graft loop could puncture the ligament, as described, supra.

DETAILED DESCRIPTION OF A PREFERRED EMBODIMENT

In order to fully disclose the present invention, reference is made herein to exemplary procedures and methods of replacing a damaged anterior cruciate ligament in the human knee. Since this exemplary reference is used to provide a context in which to explain the invention, this reference therefore is not to be construed as restricting the invention to the examples illustrated. On the contrary the invention is applicable to all obvious and equivalent variations of the method as set forth in the appended claims, and their legal equivalents.

Figure 6:
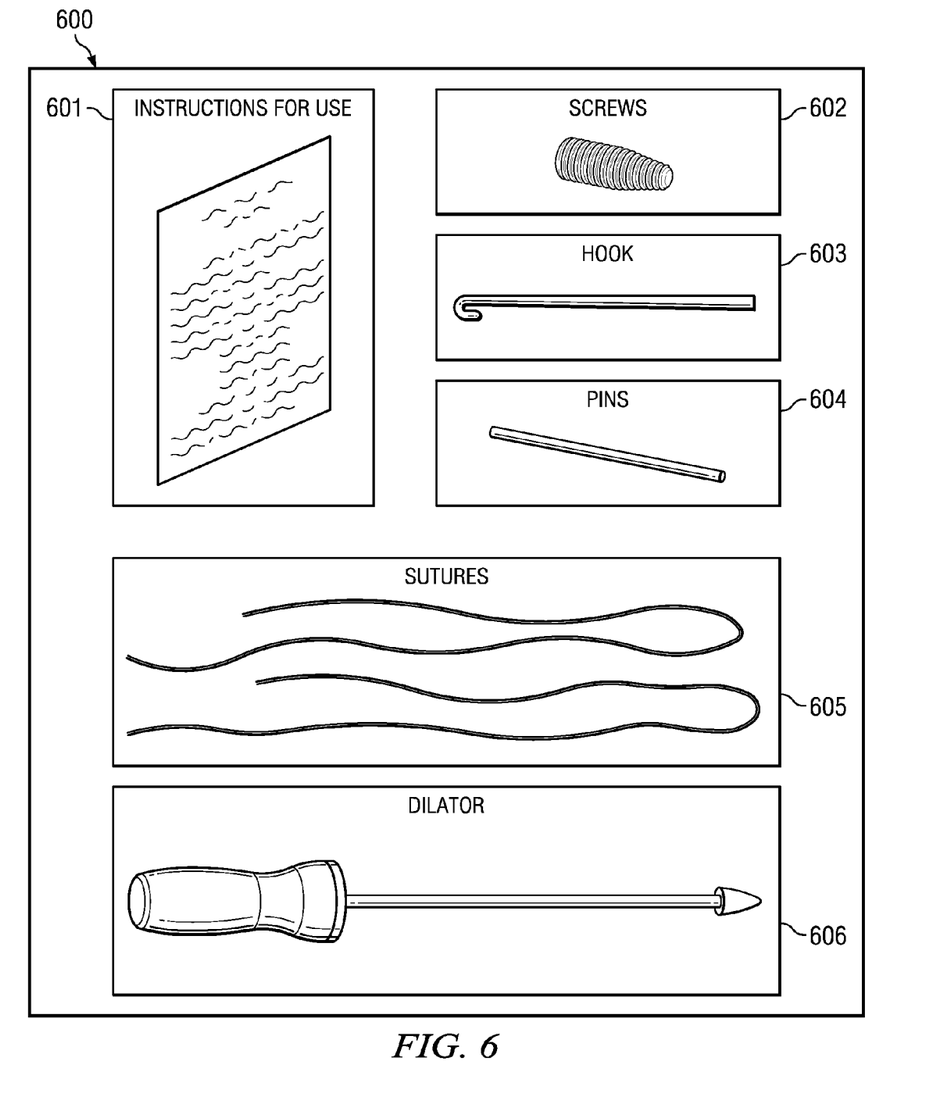
FIG. 6 is schematic representation of a surgical kit for practicing the present invention.

Referring to FIG. 6, the invention in one embodiment comprises a kit (600) that includes Instructions for Use (601), Screws (602), Hooks (603), Pins (604), Sutures (605) and Dilator (606). In one embodiment, the Instructions For Use (601) component comprises detailed description of the methods of anchoring and implanting tissues in a target location, as set forth and claimed herein. The screws, in one embodiment, include surgical screws useable for securing ligaments and tendons in surgical procedures. One such screw, for example, is the Bilok® screw available from the ArthroCare Corporation, California, USA.

Figure 7:
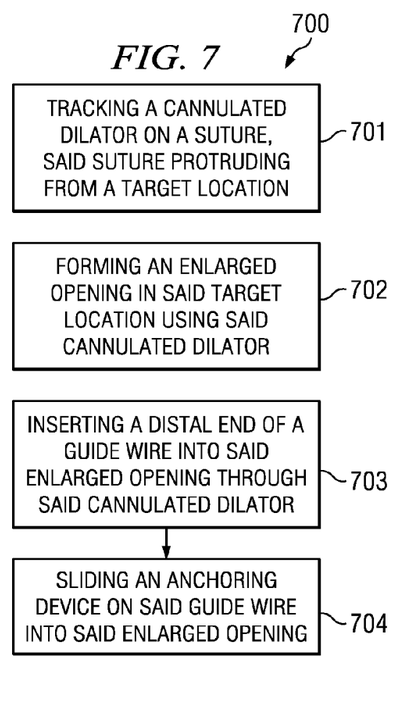
FIG. 7 is a flow chart of a method of the present invention.
Figure 9:
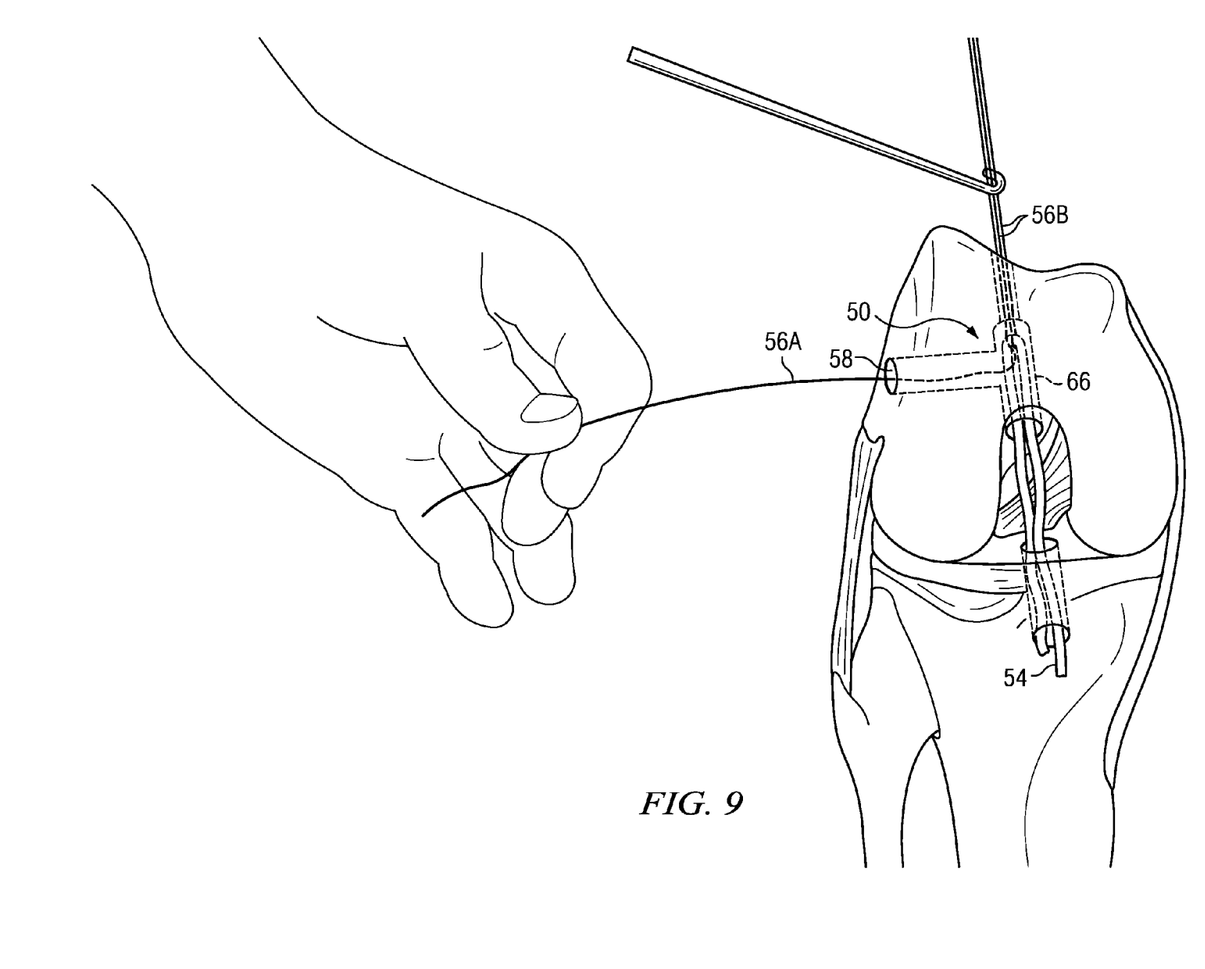
FIG. 9 depicts grabbing a section of a flexible suture from a target location in accordance with the invention.

The invention in another embodiment comprises methods of securing an anchoring device in a target location, e.g., in the knee joint as exemplified in the sequence of steps set forth in FIG. 7 and shown diagrammatically in FIGS. 9-14. In this embodiment, the invention, in step 701 comprises tracking a cannulated dilator (60) on a suture (56) protruding from the target location (50) as shown in FIG. 9. In one embodiment, the target location is a location in a condyle of a femur in a knee joint, and the tissue (54) is folded on at least two sutures (56A and 56B) and pulled into an upward tunnel (66) in the condyle of a femur. In this embodiment, the cannulated dilator is tracked on suture 56A protruding outside the knee from the target location, while the other suture (56B) holds the tissue in position inside the knee.

Figure 10:
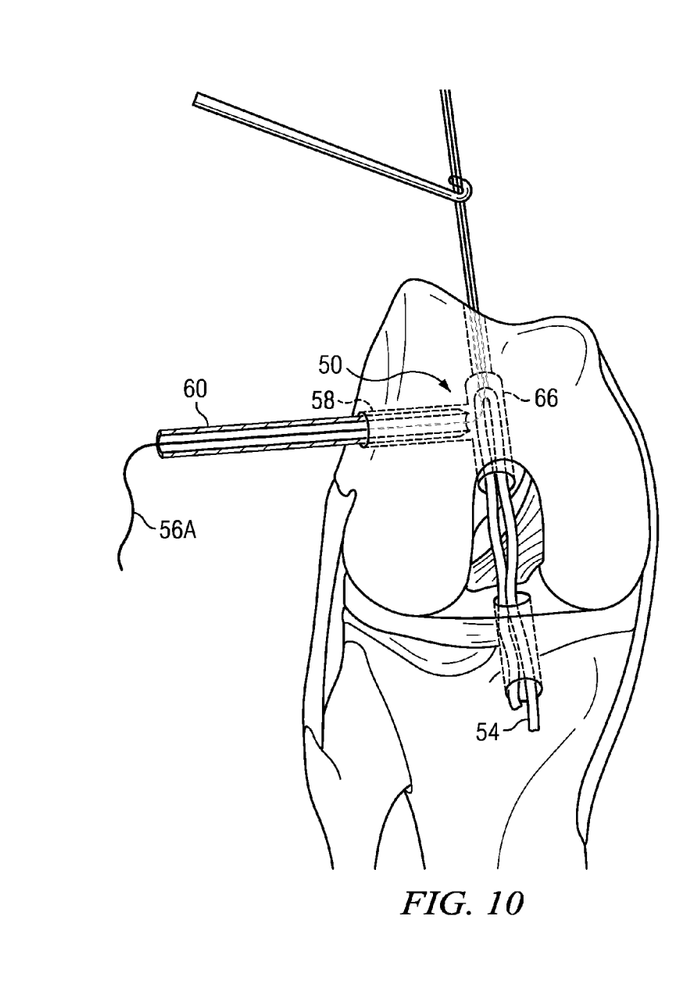
FIG. 10 depicts tracking a cannulated dilator over a flexible suture to penetrate a target location, in accordance with the invention
Figure 11:
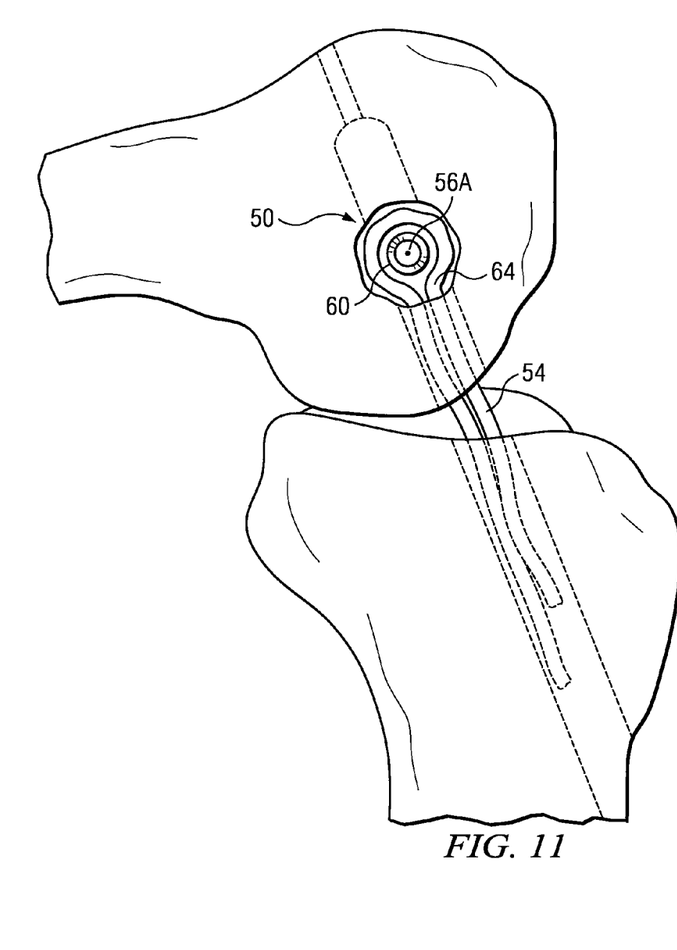
FIG. 11 depicts a side view wherein a dilator is used to enlarge a target location to form an opening therein, in accordance the invention.

In step 702, as shown in FIGS. 10 and 11, the cannulated dilator (60) while tracked on the suture (56A), is used to enlarge the opening in the fold at the kink (64) such that the enlarged opening surrounds the cannulated dilator and the suture.

Figure 12:
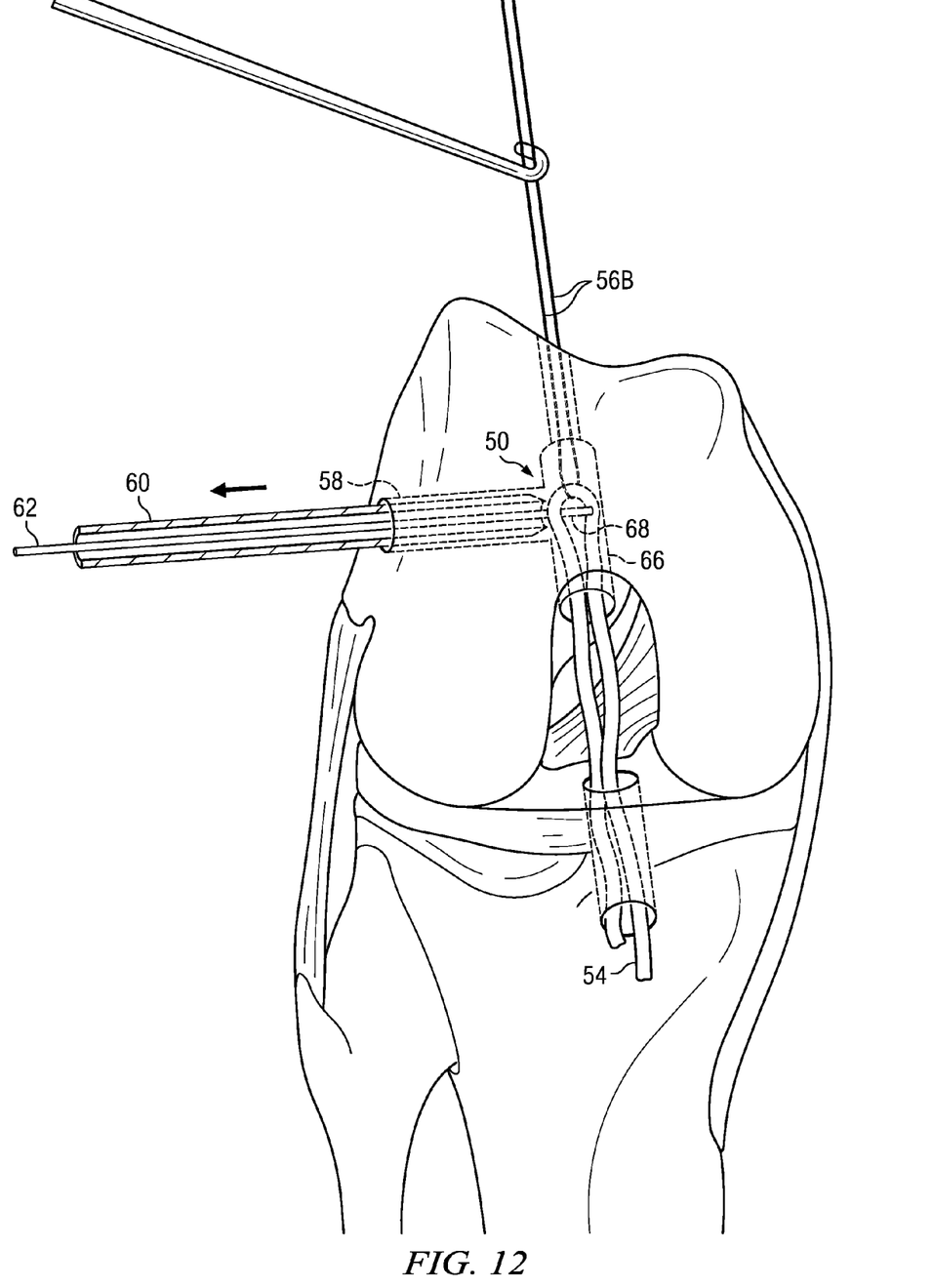
FIG. 12 depicts a step of retracting a dilator and inserting a guide wire in an enlarged opening, in accordance the invention.

In step 703, as shown in FIG. 12, the suture 56A (not shown) is removed and a guide wire (62) is delivered through the cannulated dilator such that a distal end (68) of a guide wire is inserted into the enlarged opening through the cannulated dilator.

Figure 13:
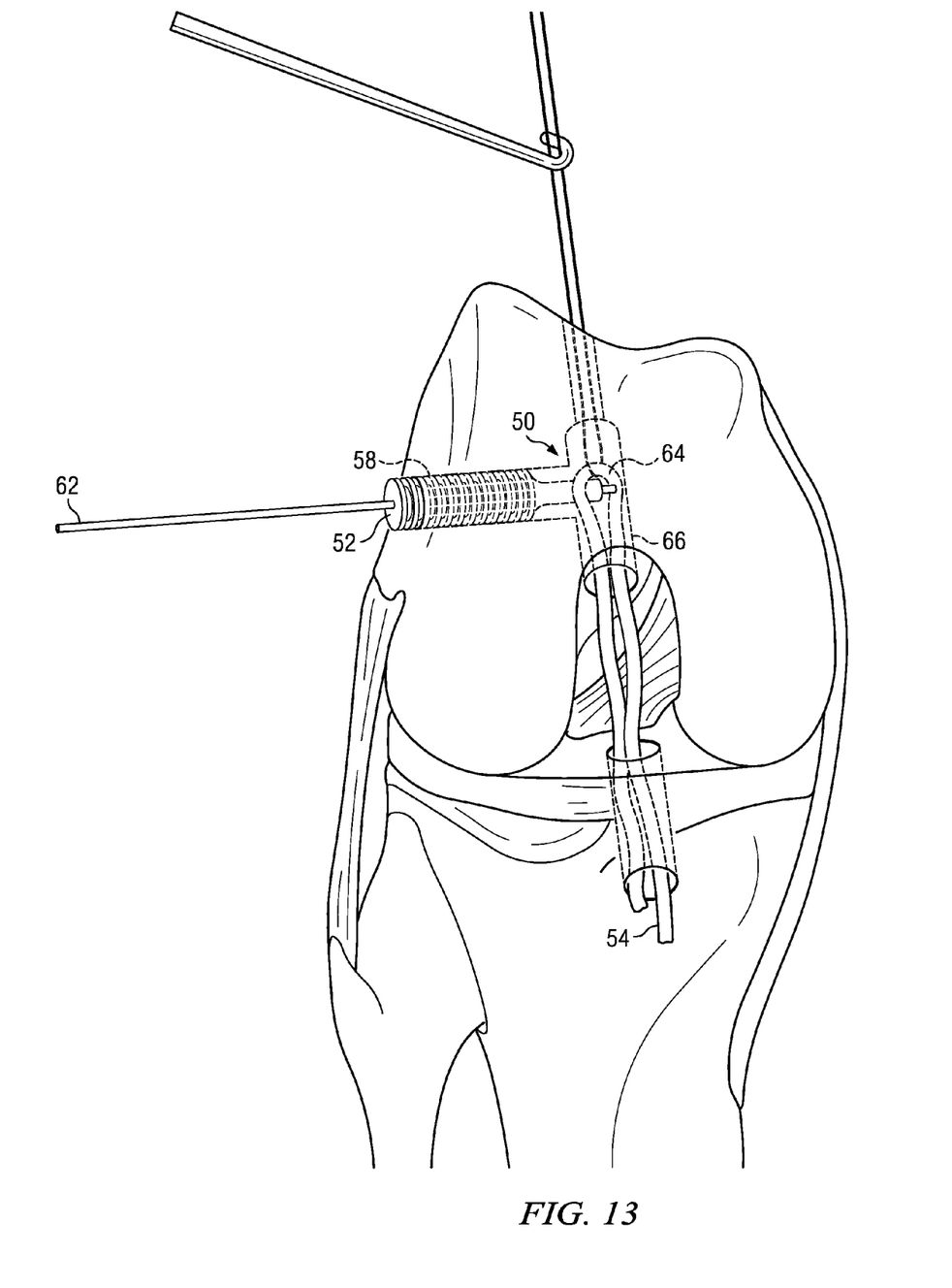
FIG. 13 depicts a step of tracking an anchoring device over a guide wire to an exemplary location in accordance the invention.
Figure 14:
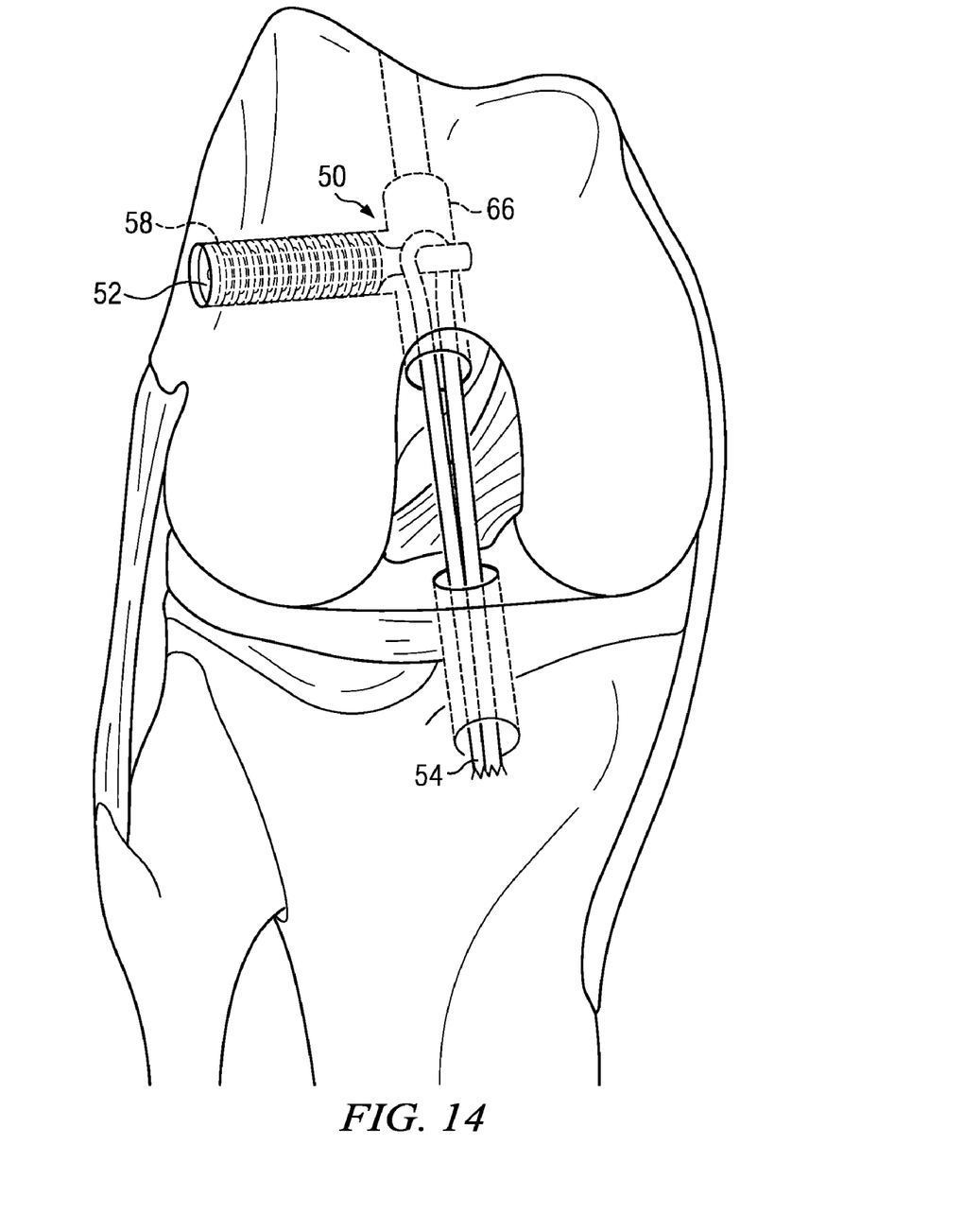
FIG. 14 depicts a target location wherein an anchoring device is used to secure a soft tissue in accordance with the invention.

In step 704, as shown in FIG. 13 the cannulated dilator is removed and an anchoring device (52) is slid over the guide wire to a position in the enlarged opening where it can be tightened to secure the tissue 54 in the condyle of a femur.

In another embodiment the invention, with reference to FIGS. 9-14, comprises grabbing a section of a flexible suture (56A) that extends from a target location (50) through a first passageway (58). In this step, grabbing involves using a tool, such as a hook, to hook, grasp, pull, withdraw, retract or otherwise obtain a section or end of the suture (56A) outside the knee. In one application the target location (50) comprises creating a tunnel within a condyle of a femur of the knee. Thereafter, a cannulated dilator (60) is tracked over the free end of the suture (56A) until the distal portion of the dilator penetrates the target location (50). While maintaining a tension on the suture (56B) to hold the tissue in position, the dilator is used to form an enlarged opening in the target location. Advantageously, the dilator tip is guided in a bull's eye manner to the target location by the guide suture. This guide suture technique avoids blindly hitting the target ligament or graft loop with an aiming instrument, which may damage the instrument. Thereafter, the suture 56A is removed while the dilator is kept in place. A guide wire is then inserted through the dilator such that the distal end of the guidewire resides, at least in part, within the opening. Thereafter, the dilator is retracted, and the an anchoring device is tracked over the guidewire such that the anchoring device is positioned, at least in part, within said opening. An example of an anchoring device is a Bilok© screw available from the ArthroCare Corporation.

Optionally the invention further comprises the steps of tightening or otherwise preparing the anchoring device in the target location. This is aided by optionally, tapping the sidewalls of the first passageway such that a screw, for example, can be used to anchor the device in, for example, a condyle of a femur. In this example, the procedure is applied to a location at the intersection of the first passageway with a second passageway in the condyle of a femur wherein the second passageway is disposed substantially transverse to the first passageway, and the second passageway is also tapped. As will be appreciated by one skilled in the art, this method can be used to define an opening within a fold of a soft tissue selected from the group consisting of tendons and ligament, as shown diagrammatically in FIG. 12 where the step of disposing the soft tissue, at least in part, is located within the second passageway.

Figure 8:
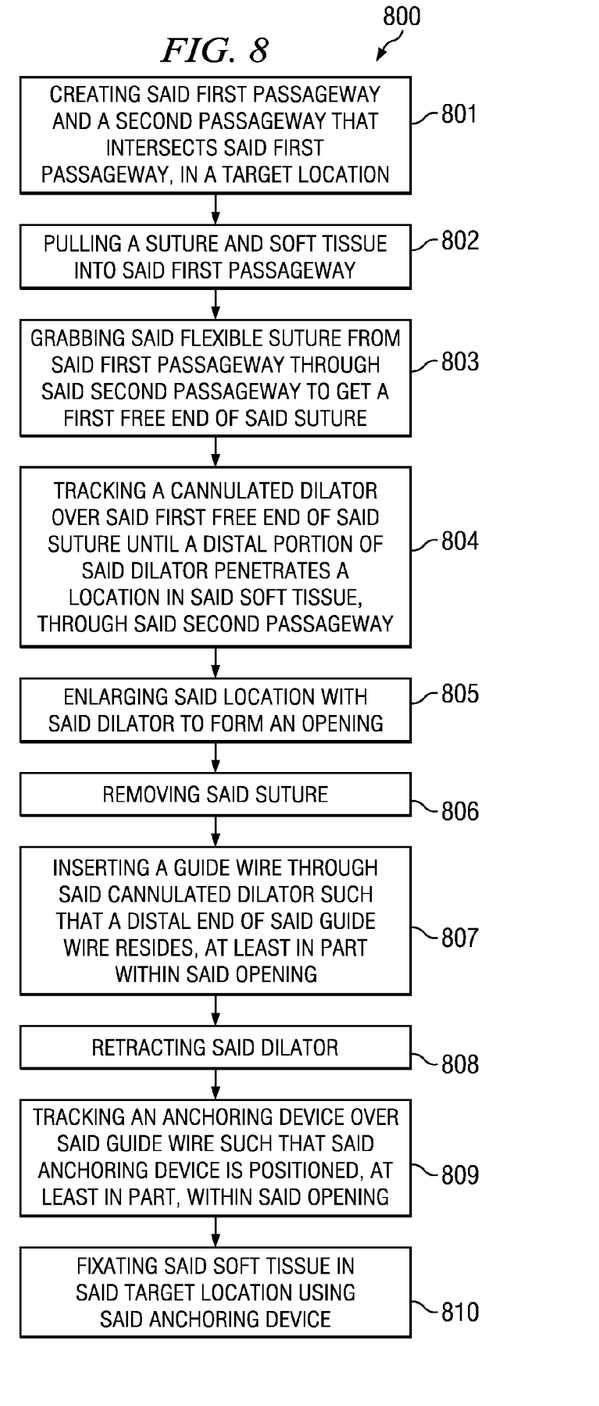
FIG. 8 is a flow chart representation of a method of the present invention.

The invention in yet another embodiment as shown in FIG. 8 comprises a surgical method of implanting soft tissue in a target location, including the step 801 whereby a first passageway is created in a the target location. Such a passageway can be can be created by drilling through the bone by methods well known in the art. In step 802, a soft tissue (54) is folded or otherwise held on a flexible suture (56A and 56B) and pulled in the first passageway (66) Soft tissue includes, for example, ligaments, tendons and artificial, biocompatible tissues. In step 803, a first free end of the flexible suture is hooked, or grabbed, or pulled from the first passageway (66) through a second passageway (58) in the target location (50).

In step 804, a cannulated dilator is tracked over the first free end of the suture (56A) until a distal portion of the dilator penetrates a location in the soft tissue, through the second passageway. In step 805, the soft tissue location is enlarged to form an enlarged opening. The suture is removed, and in step 806, a guide wire is inserted through the cannulated dilator such that a distal end of the guidewire resides, at least in part, within the enlarged opening. Thereupon, in step 807, the dilator is retracted to allow for tracking an anchoring device such as a screw over the guide wire such that the anchoring screw is positioned, at least in part, within the opening. Once in this position, the screw is useable to secure the soft tissue in the target location by tightening the screw within the second passageway. In one embodiment, the first passageways is tapped, and an implant selected from the group consisting of tendons, ligaments and artificial implants can be used to secure a soft tissue in the knee at the intersection of the first and second passageways wherein the first passageway is disposed substantially transverse to the second passageway.

Other surgical procedures may be performed in accordance with the present methods include creating bone tunnels for articular cruciate reconstructions, rotator cuff repair, and compacting, drilling, and removing hard and soft tissue in various other surgical procedures.

Thus, while the invention is described in the context of methods of securing and anchoring devices and soft tissues, it will be appreciated by one ordinarily skilled in the art that the invention can also be practiced with obvious modifications for use wherein it is desired to avoid damaging an implant or a target location. Thus the scope of the invention should not be limited to the embodiments described herein, but is limited only by the appended claims and their legal equivalents.

What is claimed is:

1. A method of surgically anchoring a device in a target location within a condyle of a femur, comprising:
   forming a first passageway in the condyle of the femur;
   forming a second passageway in the condyle of the femur, the first passageway intersecting the second passageway at the target location, the second passageway comprising an upward tunnel formed substantially transverse to the first passageway;
   pulling a first suture and a second suture attached to a tissue partially through the second passageway to the target location, the first suture and the second suture extending over a fold in the tissue;
   grabbing the second suture from the second passageway and pulling the second suture through the first passageway;
   threading the second suture through a cannulated dilator;
   tracking the cannulated dilator through the first passageway on the second suture, said second suture guiding said cannulated dilator to said target location;
   forming an enlarged opening in the fold of the tissue in said target location using said cannulated dilator, said cannulated dilator penetrating the fold of the tissue at said target location;
   inserting a distal end of a guide wire into said enlarged opening through said cannulated dilator;
   sliding an anchoring device on said guide wire into said enlarged opening.

2. The method of claim 1, further including retracting said second suture from said dilator.

3. The method of claim 1, further including withdrawing said dilator from said enlarged opening, after said inserting step.

4. The method of claim 1, further comprising removing said guidewire from said enlarged opening.

5. The method of claim 1, further comprising tightening said device in said enlarged opening.

6. The method of claim 1, wherein said enlarged opening is defined within the fold of the soft tissue selected from the group consisting of tendons and ligaments.

7. The method of claim 1, wherein said enlarged opening is defined by the intersection of said first passageway and the second passageway in said target location.

8. The method of claim 7, wherein the soft tissue is disposed in said second passageway.

9. A surgical method of securing an anchoring device in a target location, comprising:
   forming a first passageway in a condyle of a femur;
   forming a second passageway in the condyle of the femur, the first passageway intersecting the second passageway at the target location, the second passageway comprising an upward tunnel formed substantially transverse to the first passageway;
   pulling a first suture and a second suture attached to a tissue partially through the second passageway to the target location, the first suture and the second suture extending over a fold in the tissue;
   grabbing a section of the second suture in the target location, said second suture extending through the first passageway to the target location;
   tracking a cannulated instrument over a first free end of the second suture, the second suture guiding the cannulated instrument until a distal portion of the cannulated instrument penetrates the target location;
   enlarging the fold in the tissue within the target location with said instrument to form an opening therein;
   removing the suture from the cannulated instrument;
   inserting a guide wire through the cannulated instrument such that a distal end of the guidewire resides, at least in part, within the opening;
   retracting the instrument; and
   tracking an anchoring device over the guidewire such that the anchoring device is positioned, at least in part, within the opening.

10. A surgical method of implanting soft tissue in a target location, comprising:
    creating a first passageway in a condyle of a femur;
    forming a second passageway that intersects said first passageway, in a target location;
    wherein the second passageway comprises an upward tunnel formed substantially transverse to the first passageway;
    pulling a soft tissue into said second passageway;
    grabbing a suture from said second passageway through said first passageway to get a first free end of said suture;
    threading said first free end of said suture through a cannulated dilator;
    tracking the cannulated dilator over said first free end of said suture, said suture guiding said dilator until a distal portion of said dilator penetrates a fold in the soft tissue, through said first passageway;
    enlarging said fold with said dilator to form an opening;
    removing said suture;
    inserting a guide wire through said cannulated dilator such that a distal end of said guidewire resides, at least in part, within said opening;
    retracting said dilator;
    tracking an anchoring device over said guidewire such that said anchoring device is positioned, at least in part, within said opening; and securing said soft tissue in said target location using said anchoring device.

11. The method of claim 10, wherein said securing said soft tissue comprises tightening said anchoring device in said first passageway.

12. The method of claim 10, wherein said first passageway comprises tapped sidewalls.

13. The method of claim 10, wherein said anchoring device comprises a screw having a proximal threaded section and a distal tissue-support section.

14. The method of claim 10, wherein soft tissue is selected from the group consisting of tendons and ligaments.

15. The method of claim 10, wherein said anchoring device comprises an artificial implant.

\* \* \* \* \*